(12) United States Patent
McIntyre et al.

(10) Patent No.: US 9,278,228 B2
(45) Date of Patent: Mar. 8, 2016

(54) TESTING OF DEFIBRILLATOR ELECTRODES

(75) Inventors: Allister Robert McIntyre, Newtownards Co Down (GB); Johnny Houston Anderson, Holywood Co Down (GB)

(73) Assignee: HEARTSINE TECHNOLOGIES LIMITED, Belfast (GB)

( * ) Notice: Subject to any disclaimer, the term of this patent is extended or adjusted under 35 U.S.C. 154(b) by 260 days.

(21) Appl. No.: 13/480,881

(22) Filed: May 25, 2012

(65) Prior Publication Data
US 2012/0299607 A1 Nov. 29, 2012

(30) Foreign Application Priority Data

May 26, 2011 (GB) .................................. 1108875.4

(51) Int. Cl.
*G01R 31/28* (2006.01)
*A61N 1/39* (2006.01)
*A61N 1/04* (2006.01)
*A61N 1/08* (2006.01)

(52) U.S. Cl.
CPC ............... *A61N 1/3931* (2013.01); *A61N 1/046* (2013.01); *A61N 2001/083* (2013.01)

(58) Field of Classification Search
CPC .. G01R 33/288; G01R 33/285; G01R 33/286; G01R 33/4806
USPC ...................... 607/5–8, 142, 115; 324/750.01
See application file for complete search history.

(56) References Cited

U.S. PATENT DOCUMENTS

| | | | | |
|---|---|---|---|---|
| 4,153,049 | A * | 5/1979 | Gatzke et al. | 607/5 |
| 5,645,571 | A * | 7/1997 | Olson | A61N 1/39 |
| | | | | 607/142 |
| 5,797,969 | A | 8/1998 | Olson et al. | |
| 6,694,193 | B2 * | 2/2004 | Lyster et al. | 607/142 |
| 6,904,314 | B1 | 6/2005 | Brewer et al. | |
| 8,668,643 | B2 * | 3/2014 | Kinast | A61B 5/0031 |
| | | | | 600/300 |
| 2003/0032988 | A1 | 2/2003 | Fincke | |
| 2005/0277991 | A1 | 12/2005 | Covey et al. | |
| 2006/0142806 | A1 * | 6/2006 | Katzman et al. | 607/5 |
| 2008/0177341 | A1 * | 7/2008 | Bowers | 607/5 |

(Continued)

FOREIGN PATENT DOCUMENTS

GB 2386071 A1 9/2003
WO 2004073797 A1 9/2004

*Primary Examiner* — Alesa Allgood
(74) *Attorney, Agent, or Firm* — Novak Druce Connolly Bove + Quigg LLP

(57) ABSTRACT

Systems and methods for testing defibrillator electrode conductivity. Connection for electrically connecting electrodes and defibrillation signal generator connected to the electrodes. Patient impedance measurement system comprising patient signal generator and patient signal receiver. A defibrillator controller connected to defibrillation signal generator and patient impedance measurement system. An electrode test system with control signal device connected to the patient signal receiver which generates at least one control signal causing the patient signal receiver to change from a patient signal receive state to an electrode test signal receive state, a test commence signal device connected to the patient signal generator which generates at least one test commence signal causing the patient signal generator to send a test signal to the electrodes and an electrode test signal device connected to the patient signal receiver which receives an electrode test signal and processes the signal to determine a test result.

18 Claims, 1 Drawing Sheet

(56) References Cited

U.S. PATENT DOCUMENTS

2008/0288011 A1* 11/2008 Katzman et al. .................. 607/5
2012/0191152 A1* 7/2012 Kameli .................. A61N 1/375
607/7

* cited by examiner

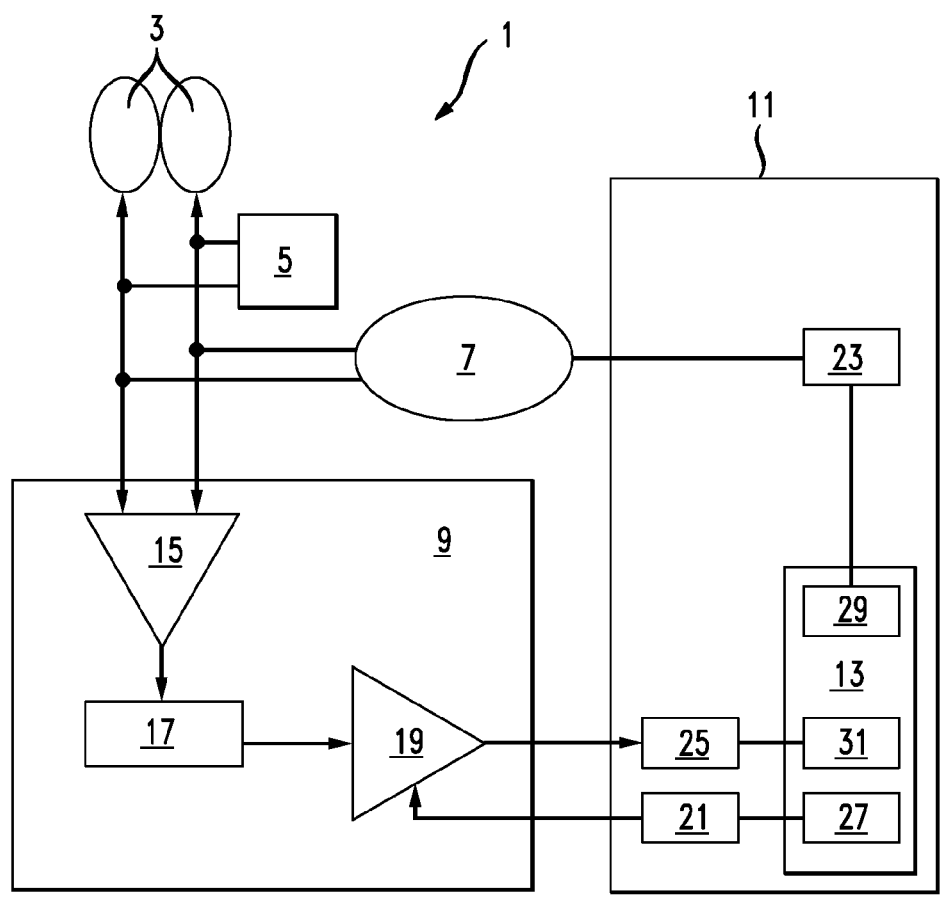

TESTING OF DEFIBRILLATOR ELECTRODES

This application claims priority under 35 U.S.C. §119 to United Kingdom Patent Application No. 1108875.4 filed May 26, 2011, the entire disclosure of which is herein expressly incorporated by reference.

This invention relates to testing of electrodes for defibrillators, and particularly to the testing of the electrical integrity of the electrodes, i.e. the ability of the electrodes to conduct an electrical signal.

Defibrillators are used to provide a 'shock', i.e. electrical signals, to a patient's heart. Studies have shown that the efficacy of a shock decreases significantly as time from the cardiac arrest increases. It is therefore important to use a defibrillator to apply electrical signals to the patient's heart as quickly as possible. This being the case, defibrillators are now frequently found in various public locations, not just in hospitals. In many such locations, a defibrillator may not be used for substantial periods of time. The defibrillator electrodes will usually remain in their packaging during this time. It is crucial that the electrical integrity of the defibrillator electrodes is maintained over these periods, or, if the integrity is compromised, that this information is made available to a potential user of the defibrillator. This is particularly the case when a defibrillator may be used by a member of the public with little or no experience of defibrillator technology or operation. It is therefore desirable to provide defibrillators with a means by which the integrity of the electrodes may be tested.

BRIEF DESCRIPTION OF THE DRAWINGS

FIG. 1 illustrates an exemplary defibrillator embodiment.

According to a first aspect of the invention there is provided a defibrillator comprising electrodes,
a connection for electrically connecting the electrodes together during a test,
a defibrillation signal generator, connected to the electrodes,
a patient impedance measurement system, connected to the electrodes, comprising a patient signal generator and a patient signal receiver,
a defibrillator controller connected to the defibrillation signal generator and the patient impedance measurement system, and
an electrode test system, comprising
a control signal device, connected to the patient signal receiver, which generates at least one control signal which causes the patient signal receiver to change from a patient signal receive state to an electrode test signal receive state,
a test commence signal device, connected to the patient signal generator, which generates at least one test commence signal which causes the patient signal generator to send a test signal to the electrodes, and
an electrode test signal device, connected to the patient signal receiver, which receives an electrode test signal and processes the signal to determine a pass test result or a fail test result for the electrodes.

When applying defibrillation signals to a patient's heart, it is important to take into consideration the impedance of the patient, as this varies from person to person, e.g. between 20Ω and 300Ω, and will determine the energy of the defibrillation signals. Many defibrillators therefore provide patient impedance measurement systems. These systems apply an ac signal to the electrodes, when these are attached to the patient, measure an ac signal from the electrodes and use this to calculate the impedance of the patient.

In the present invention, a test system is provided for the electrodes of a defibrillator. This uses the components of the patient impedance measurement system to apply a test signal to the electrodes and measure a resulting test signal from the electrodes. Thus testing of the electrodes' electrical integrity is carried out using equipment already present in the defibrillator, reducing costs etc. of providing the defibrillator with an electrode test capability.

The control signal device may comprise control signal software which operates with a signal generator of the defibrillator to generate the at least one control signal. The control signal software may be implemented in the defibrillator controller. The control signal device may comprise control signal software and a control signal generator, and the control signal software may operate with the control signal generator to generate the at least one control signal.

The control signal device may generate at least one control signal which causes the patient signal receiver to modify one or more characteristics thereof to change from a patient signal receive state to an electrode test signal receive state. The control signal device may generate at least one control signal which causes the patient signal receiver to modify a gain characteristic thereof. The patient signal receiver may comprise an amplifier, and the control signal device may generate a control signal which causes the amplifier to modify a gain characteristic thereof. The amplifier may comprise a voltage-controlled amplifier, and the control signal device may generate a control signal comprising a voltage signal which causes the amplifier to modify a gain characteristic thereof. The amplifier may comprise a resistance-controlled amplifier, connected to a switch, and the control signal device may generate a control signal comprising a logic signal sent to the switch which causes the amplifier to modify a gain characteristic thereof.

The control signal device may initiate generation of the at least one control signal on receipt of a test initiation signal. The control signal device may comprise a control signal receiver which receives the test initiation signal. The control signal device may receive a test initiation signal from the defibrillator controller on determination by the controller that an electrode test is required, for example as part of an automatic defibrillator self-check process. The test initiation device may receive a test initiation signal from a test initiator, for example a button or switch, provided on the defibrillator.

The test commence signal device may comprise test commence signal software which operates with a signal generator of the defibrillator to generate the at least one test commence signal. The test commence signal software may be implemented in the defibrillator controller. The test commence signal device may comprise test commence signal software and a test commence signal generator, and the test commence signal software may operate with the test commence signal generator to generate the at least one test commence signal.

The test commence signal may cause the patient signal generator to send a test signal to the electrodes having the same characteristics as a signal sent to the electrodes to measure the impedance of the patient. The test commence signal may cause the patient signal generator to send an ac test signal to the electrodes having a frequency of, for example, approximately 30 kHz.

The test commence signal device may initiate generation of the at least one test commence signal on receipt of a test initiation signal. The test commence signal device may comprise a test commence signal receiver which receives the test initiation signal. The test commence signal device may receive a test initiation signal from the control signal device. The test commence signal device may receive a test initiation signal from the defibrillator controller on determination by the controller that an electrode test is required, for example as part of an automatic defibrillator self-check process. The test commence signal device may receive a test initiation signal from a test initiator, for example a button or switch, provided on the defibrillator.

The electrode test signal device may comprise electrode test signal software which operates with a signal receiver of the defibrillator to receive the electrode test signal. The electrode test signal software may be implemented in the defibrillator controller. The electrode test signal device may comprise electrode test signal software and an electrode test signal receiver, and the electrode test signal software may operate with the electrode test signal receiver to receive the electrode test signal.

The electrode test signal device may process the electrode test signal to obtain a measure of the impedance of the electrodes and use this to determine the test result of the electrodes. The electrode test signal device may receive an electrode test signal comprising an electrode voltage signal, and process the electrode voltage signal using a look-up table of electrode voltage versus electrode impedance to obtain a measure of the impedance of the electrodes. The electrode test signal device may receive an electrode test signal comprising an electrode voltage signal, and process the electrode voltage signal by using it to calculate a measure of the impedance of the electrodes. The electrode test signal device may receive an electrode test signal comprising an electrode voltage signal, and process the electrode voltage signal using a fixed value comparator to determine a measure of the impedance of the electrodes. The electrode test signal device may set a threshold for the electrode impedance, compliance with which gives a pass test result of the electrodes and non-compliance with which gives a fail test result of the electrodes. The threshold may comprise a single value of the impedance of the electrodes, above which a pass test result of the electrodes is determined and below which a fail test result of the electrodes is determined. The threshold may comprise, for example, a value of 1 kΩ for the impedance of the electrodes. The threshold may comprise a range of values of the impedance of the electrodes within which a pass test result of the electrodes is determined and outside which a fail test result of the electrodes is determined. The threshold may comprise, for example, a range of 1 kΩ to 5 kΩ for the impedance of the electrodes.

The electrode test signal device may process the electrode test signal to measure the voltage of the electrodes and use the electrode voltage to determine the test result of the electrodes. The electrode test signal device may set a threshold for the electrode voltage, compliance with which gives a pass test result of the electrodes and non-compliance with which gives a fail test result of the electrodes. The threshold may comprise a single value of the voltage of the electrodes, above which a pass test result of the electrodes is determined and below which a fail test result of the electrodes is determined. The threshold may comprise, for example, a value of 1.5 V of the voltage of the electrodes. The threshold may comprise a range of values of the voltage of the electrodes, within which a pass test result of the electrodes is determined and outside which a fail test result of the electrodes is determined. The threshold may comprise, for example, a range of 1.5 to 2 V of the voltage of the electrodes.

The electrode test signal device may determine a pass test result of the electrodes and send a signal to the defibrillator controller which causes it to allow generation of defibrillation signals. The electrode test signal device may determine a fail test result of the electrodes and send a signal to the defibrillator controller which causes it to prevent generation of defibrillation signals. The electrode test signal device may determine a fail test result of the electrodes and issue a warning indicating the fail test result. The warning may be an audible warning. The warning may be a visible warning, such as activation of a warning light provided on the defibrillator.

The connection for electrically connecting the electrodes together during a test may be provided by packaging in which the electrodes are stored. The packaging may provide a conductive path from one electrode to the other electrode. The conductive path may be achieved by providing apertures in packaging liners covering gel provided on the electrodes, such that, when placed in the packaging, the electrodes are connected via the exposed gel.

According to second aspect of the invention there is provided a method of testing electrical conductivity of electrodes of a defibrillator comprising connecting the electrodes together during a test, generating at least one control signal which causes a patient signal receiver of a patient impedance measurement system of the defibrillator to change from a patient signal receive state to an electrode test signal receive state, generating at least one test commence signal which causes a patient signal generator of the patient impedance measurement system to send a test signal to the electrodes, and receiving an electrode test signal from the patient signal receiver and processing the signal to determine a pass test result or a fail test result for the electrodes.

Electrode tests may be carried out at regular intervals, for example once a week, or once a month, or may be carried out before application of a shock to a patient, or may be carried out on power-up of the defibrillator.

An embodiment of the invention will now be described, by way of example only, with reference to the accompanying drawing, which is a schematic representation of a defibrillator according to the first aspect of the invention.

Referring to the drawing, this shows a defibrillator 1 comprising electrodes 3, a connection for electrically connecting the electrodes together during a test (not shown), a defibrillation signal generator 5, a patient impedance measurement system comprising a patient signal generator 7 and a patient signal receiver 9, a defibrillator controller 11 and an electrode test system 13. The patient signal receiver 9 comprises a differential amplifier 15, a filter 17 and an amplifier/rectifier 19. The defibrillator controller 11 comprises a first signal generator 21, a second signal generator 23 and a signal receiver 25. The electrode test system 13 comprises a control signal device 27, a test commence signal device 29 and an electrode test signal device 31. In this embodiment, the defibrillator 1 further comprises a battery (not shown) which provides power for the components of the defibrillator. The various components of the defibrillator 1 are connected together as shown in the drawing, for sending and receiving electrical signals between the components. It will be appreciated that other connections which are not shown may be provided between the components of the defibrillator 1.

In this embodiment, the components of the electrode test system 13 are implemented in software in the defibrillator controller 11. The control signal device 27 comprises control signal software which operates with the first signal generator 21 of the defibrillator controller 11. The test commence signal device 29 comprises test commence signal software which operates with the second signal generator 23 of the defibrillator controller 11. The electrode test signal device 31 comprises electrode test signal software which operates with the signal receiver 25 of the defibrillator controller 11. The control signal device 27, the test commence signal device 29 and the electrode test signal device 31 are shown as separate components. These can be implemented in separate software modules in the controller 11, but it will be appreciated that these can be also be implemented in one software module in the controller 11. It will be further appreciated that the control signal device 27, the test commence signal device 29 and the electrode test signal device 31 may be implemented in a memory unit which is separate to and connected with the controller 11.

The defibrillator 1 is used to apply defibrillation signals to a patient's heart. To do this, the defibrillator 1 is powered up and the electrodes 3 are applied to the patient's chest. The patient impedance measurement system is first used to measure the transthoracic impedance of the patient. This is required in order to deliver the correct energy of defibrillation signals to the patient. The defibrillator controller 11 causes the patient signal generator 7 to be operated in order to apply a signal to the electrodes 3. The patient signal generator 7 comprises a high impedance ac signal generator and applies an ac current signal having a frequency of approximately 30 kHz to a first electrode 3, through the patient's chest, to the remaining electrode 3. The electrodes 3 output an ac voltage signal to the differential amplifier 15 of the patient signal receiver 9. The amplifier 15 outputs an ac voltage signal which is proportional to the difference between the voltages on the electrodes and passes this ac voltage signal to the filter 17. The filter 17 is configured as a band pass filter and attenuates unwanted frequencies in the ac voltage signal and accentuates the frequency of interest, i.e. 30 kHz. The filtered ac voltage signal is output to the amplifier/rectifier 17, which rectifies the ac voltage signal producing a dc voltage signal and amplifies this signal to produce a dc voltage signal which is compatible with the input requirements of the controller 11. The dc voltage signal is passed to the controller 11, which uses it to obtain the impedance of the patient. The controller 11 then sends a control signal to the defibrillation signal generator 5, which causes the generator 5 to generate defibrillation signals of an appropriate energy which are then applied to the electrodes 3 and the patient.

In order to apply defibrillation signals to the patient, the electrodes 3 must have electrical integrity, i.e. the ability to conduct an electrical signal. This is determined by testing the electrical conductivity of the electrodes using the electrode test system 13. This uses the components of the patient impedance measurement system to apply a test signal to the electrodes 3 and measure a resulting test signal from the electrodes 3. Thus testing of the electrodes' electrical integrity is carried out using equipment already present in the defibrillator 1.

In this embodiment, the electrode test is effected by determining a measure of the impedance of the electrodes 3. The electrode impedance should be in the range of approximately 1 kΩ to 5 kΩ when the electrical integrity of the electrodes is acceptable, and greater than 5 kΩ when the electrical integrity of the electrodes has been impaired. The impedance of a patient is usually in the range 20Ω to 300Ω. In use of the defibrillator 1, the patient signal receiver 9 is configured to be able to receive signals having an impedance in the patient impedance range. When the electrodes 3 of the defibrillator 1 are tested, the patient signal receiver 9 must be configured to be able to receive signals having an impedance in the electrode impedance range, which is much greater than the patient impedance range. It is therefore necessary for the patient signal receiver 9 to change from a patient signal receive state to an electrode test signal receive state.

The electrodes 3 are electrically connected together during the test. In this embodiment, the connection for the electrodes is provided by packaging in which the electrodes are stored. The packaging provides a conductive path from one electrode to the other electrode. The conductive path is achieved by providing apertures in packaging liners covering gel provided on the electrodes, such that, when placed in the packaging, the electrodes are connected via the exposed gel. It will be appreciated, however, that other connection means may be used to electrically connect the electrodes together.

The electrode test system 13 operates as follows. The defibrillator controller 11 determines that an electrode test is required (for example using a timer) as part of an automatic defibrillator self-check process. The defibrillator controller 11 instructs the components of the defibrillator 1 to power on. (In this embodiment, each of the components of the defibrillator 1 is switched on, but it will be appreciated that only some of the components may be switched on, e.g. only those required to carry out the electrode test). The defibrillator controller 11 communicates initiation of the electrode test to the control signal generator 27. This comprises control signal software which operates with the first signal generator 21 of the controller 11 to generate a control signal which is sent to the amplifier/rectifier 19 of the patient signal receiver 9. The amplifier/rectifier 19 comprises a voltage-controlled amplifier, and the control signal comprises a voltage signal which causes the amplifier to modify a gain characteristic thereof, thus causing the patient signal receiver 9 to change from a patient signal receive state to an electrode test signal receive state.

The defibrillator controller 11 then communicates initiation of the electrode test to the test commence signal device 29. This comprises test commence signal software which operates with the second signal generator 23 of the controller 11 to generate a test commence signal which is sent to the patient signal generator 7. This causes the patient signal generator 7 to send a test signal to the electrodes 3. The test signal has the same characteristics as a signal sent to the electrodes 3 to measure the impedance of the patient, i.e. an ac current signal having a frequency of approximately 30 kHz.

An electrode test signal, comprising an ac voltage signal, is generated in the electrodes 3 and this is received by the patient signal receiver 9. The electrode test signal is processed by the components of the patient signal receiver 9 in the same way as the patient signal, see above. The electrode test signal device 31 comprises electrode test signal software which operates with the receiver 25 of the controller 11 to receive the electrode test signal from the patient signal receiver 9. The electrode test signal, comprising a dc voltage signal, is processed by the electrode test signal device 31 to obtain a measure of the impedance of the electrodes. In this embodiment, the electrode test signal device 31 uses a look-up table of voltage versus impedance to get a measure of the electrode impedance. This is then used to determine a test result of the electrodes 3. The electrode test signal device 31 sets a threshold range for the electrode impedance of approximately 1 kΩ to approximately 5 kΩ, within and below which a pass test result of the electrodes 3 is determined and above which a fail test result of the electrodes 3 is determined. When the electrode test signal device 31 determines a pass test result of the electrodes 3, it communicates this to the defibrillator controller 11 which then allows generation of defibrillation signals by the defibrillation signal generator 5. A pass test result determines that the electrical integrity of the connection to each electrode is intact and that there is a high probability that the electrode construction is within specification. When the electrode test signal device 31 determines a fail test result of the electrodes 3, it communicates this to the defibrillator controller 11 which prevents generation of defibrillation signals. The defibrillator 1 may also issue a warning indicating the fail test result, such as an audible warning and/or a visible warning e.g. activation of a warning light provided on the defibrillator 1.

The invention claimed is:

1. A defibrillator system comprising:
a pair of electrodes, configured to be separate from one another but in direct electrical contact with a patient when in an electrode defibrillation condition for performing defibrillation of the patient, and configured to be electrically connected together while not in direct contact with the patient when in an electrode storage condition for storing the pair of electrodes prior to defibrillation;
a defibrillation signal generator, connected with the pair of electrodes, for providing a defibrillation shock at a controlled electrical defibrillation output value to a patient;
a controller device; and
a non-transitory memory having instructions stored which, when executed by the controller device, cause the controller device to perform operations comprising, when the pair of electrodes is in an electrode storage condition:
setting a gain characteristic of an amplifier in the controller device at a first gain value to process signals for the performing of defibrillation of the patient; and
upon determining a test of the pair of electrodes should occur:
modifying the gain characteristic of the amplifier to a second gain value which is distinct from the first gain value, wherein the second gain value is for processing signals while in the electrode test signal receive state;
sending an electrode integrity test signal to the pair of electrodes in the electrode storage condition;
processing the electrode integrity test signal result using the second gain value; and
when the electrode integrity test signal result indicates degradation of the pair of electrodes, issuing a warning, wherein the degradation is indicated by the electrode integrity test signal result having an impedance outside a threshold range.

2. The defibrillator system of claim 1, wherein an electrical integrity of the electrode integrity test signal result is representative of an electrical impedance value for the pair of electrodes.

3. The defibrillator system of claim 1, further comprising:
an electrode storage packaging for storage of the pair of electrodes comprising an electrically-insulative packaging liner having at least one or more apertures provided therein,
wherein each of the pair of electrodes comprises an electrode layer and at least one conductive gel surface disposed over the electrode layer; and
when the pair of electrodes are in the electrode storage condition, the pair of electrodes are disposed within the electrode storage packaging and each configured with the at least one conductive gel surface in proximity to one another, and the packaging liner is disposed between each of the at least one conductive gel surface to provide an electrical connection between the pair of electrodes.

4. The defibrillator system of claim 1, the non-transitory memory further including instructions stored which, when executed by the controller, result in operations comprising preventing a defibrillation shock from being sent by the defibrillation signal generator when the degradation of the electrical integrity of the pair of electrodes is indicated by the electrode integrity test signal result.

5. The defibrillator system of claim 1, wherein sending of the electrode integrity test signal, and the setting of the gain characteristic, occur periodically.

6. The defibrillator system of claim 5, wherein sending of the electrode integrity test signal occurs during power-up of the defibrillator system.

7. The defibrillator system of claim 5, wherein sending of the electrode integrity test signal occurs prior to delivery of a defibrillation shock to the patient.

8. The defibrillator system of claim 1, further comprising:
a patient impedance measurement system, connected to the pair of electrodes, for measuring an electrical impedance of the patient when the pair of electrodes are in the electrode defibrillation condition, the patient impedance measurement system comprising:
a patient signal generator for generating a patient impedance test signal to the pair of electrodes, and;
a patient signal receiver for receiving a patient impedance test signal result from the pair of electrodes;
a defibrillator controller connected to the defibrillator signal generator and patient impedance measurement system for controlling the electrical defibrillation output at a value based upon the patient impedance test signal result; and
the non-transitory memory further including additional instructions stored which, when executed by the controller, result in operations comprising:
identifying, based on the electrical impedance, that the pair of electrodes are in the electrode defibrillation condition; and
subsequent to identifying that the pair of electrodes are in the electrode defibrillation condition:
sending the patient impedance test signal to the pair of electrodes;
receiving the patient impedance test signal result in response to the patient impedance test signal, the patient impedance test signal result indicating an electrical impedance value of the patient; and
sending a defibrillation shock by the defibrillator signal generator, based upon the patient impedance test signal result, through the pair of electrodes to the patient.

9. The defibrillator system of claim 8, the patient signal receiver further comprising an amplifier coupled to the pair of electrodes and the defibrillator signal generator for modifying a gain characteristic based upon the patient impedance test signal result.

10. A method comprising:
setting a gain characteristic of an amplifier at a first gain value to process signals for performing a defibrillation of a patient via a defibrillator;
modifying the gain characteristic of the amplifier to a second gain value for processing signals in an electrode test signal receive state, to yield a modified gain characteristic;
sending an electrode integrity test signal to the pair of electrodes to provide an electrode integrity test signal result based on a detected impedance value associated with an electrical integrity of the pair of electrodes;
processing an electrode integrity test signal result using the modified gain characteristic; and when the electrode integrity test signal result indicates a degradation of the pair of electrodes, issuing a warning, wherein the degradation is indicated by the electrode integrity test signal result having an impedance outside a threshold range.

11. The method of claim 10, wherein the electrode integrity test signal is sent periodically.

12. The method of claim 10, wherein the electrode integrity test signal is sent during power-up of the defibrillator system.

13. The method of claim 10, wherein the electrode integrity test signal is sent prior to delivery of a defibrillation shock to the patient.

14. The method of claim 10, further comprising preventing a defibrillation shock from being sent by the defibrillator when the degradation of the pair of electrodes is indicated by the integrity test signal result.

15. The method of claim 10, further comprising:
identifying, based on the electrical impedance, that the pair of electrodes are in an electrode defibrillation condition; and
subsequent to identifying that the pair of electrodes are in the electrode defibrillation condition:
sending a patient impedance test signal to a patient for providing a patient impedance test signal which is indicative of an electrical impedance value of the patient;
receiving the patient impedance test signal in response to the impedance test signal; and
sending a defibrillation shock through the pair of electrodes to the patient, wherein a value of the defibrillation shock varies as a function of the value of the patient impedance test signal result.

16. The method of claim 10, wherein an electrode storage condition comprises the pair of electrodes and an electrically-insulative packaging liner disposed therebetween, and wherein the electrically-insulative packaging liner further comprises at least one or more apertures provided therein to provide an electrical connection between the pair of electrodes.

17. The method of claim 16, wherein the electrical connection provided between the pair of electrodes further comprises:
(a) providing a conductive gel surface over an electrically-conductive portion of each of the pair of electrodes; and
(b) arranging the conductive gel surface for each of the pair of electrodes into direct contact with the electrically-insulative packaging liner disposed therebetween.

18. A method comprising:
setting a gain characteristic of an amplifier in a defibrillator system to a first gain value for processing signals during performing of defibrillation of a patient;
when a pair of electrodes in the defibrillator system is in an electrode storage condition indicating that the pair of electrodes is not in direct contact with a patient: setting the gain characteristic of the amplifier in the defibrillator system to a second gain value for processing signals in an electrode test signal receive state; and
sending an electrode integrity test signal to the pair of electrodes to yield an electrode integrity test signal result;
processing the electrode integrity test signal result using the amplifier set at the second gain value, to yield a processed signal; and
when the processed signal indicates degradation of the pair of electrodes, issuing a warning, wherein the degradation is indicated by the electrode integrity test signal result having an impedance outside a threshold range.

* * * * *